United States Patent
Candiani et al.

(10) Patent No.: US 12,359,157 B2
(45) Date of Patent: Jul. 15, 2025

(54) DEVICE, METHOD AND COMPOSITION FOR TRANSFECTION OF CELLS WITH NUCLEIC ACIDS

(71) Applicant: POLITECNICO DI MILANO, Milan (IT)

(72) Inventors: Gabriele Candiani, Milan (IT); Nina Bono, Sciacca (IT); Federica Ponti, Induno Olona (IT)

(73) Assignee: POLITECNICO DI MILANO, Milan (IT)

( * ) Notice: Subject to any disclaimer, the term of this patent is extended or adjusted under 35 U.S.C. 154(b) by 0 days.

(21) Appl. No.: 17/999,445

(22) PCT Filed: May 21, 2021

(86) PCT No.: PCT/EP2021/063610
§ 371 (c)(1),
(2) Date: Nov. 21, 2022

(87) PCT Pub. No.: WO2021/234136
PCT Pub. Date: Nov. 25, 2021

(65) Prior Publication Data
US 2023/0120357 A1    Apr. 20, 2023

(30) Foreign Application Priority Data
May 22, 2020    (IT) .............................. 102000000012055

(51) Int. Cl.
*C12M 1/42*        (2006.01)
*C12N 13/00*       (2006.01)
*C12N 15/88*       (2006.01)

(52) U.S. Cl.
CPC ............. *C12M 35/04* (2013.01); *C12N 13/00* (2013.01); *C12N 15/88* (2013.01)

(58) Field of Classification Search
None
See application file for complete search history.

(56) References Cited

FOREIGN PATENT DOCUMENTS

| CN | 103553970 A | 2/2014 | |
|----|----|----|----|
| EP | 1944080 A1 * | 7/2008 | .......... B01F 11/0002 |
| WO | 2000003683 A2 | 1/2000 | |
| WO | WO-2006027602 A1 * | 3/2006 | .......... B01F 11/0266 |

(Continued)

OTHER PUBLICATIONS

Villate-Beitia et al. "Non-viral vectors based on magnetoplexes, lipoplexes and polyplexes for VEGF gene delivery into central nervous system cells." International Journal of Pharmaceutics 521 (2017) 130-140. (Year: 2017).*

(Continued)

*Primary Examiner* — William H. Beisner
(74) *Attorney, Agent, or Firm* — Silvia Salvadori, P.C.; Silvia Salvadori

(57) ABSTRACT

Disclosed are a method, a composition and a device for the introduction of exogenous nucleic acids into eukaryotic cells by non-viral vectors (non-viral transfection). The method according to the invention is based on application of a high-frequency oscillatory motion to a solution containing nucleic acids and cationic polymers or lipids to obtain particles (complexes) with high transfection efficiency.

13 Claims, 6 Drawing Sheets

(56) References Cited

FOREIGN PATENT DOCUMENTS

WO      WO-2015052403 A1 *   4/2015   ......... B01F 11/0014

OTHER PUBLICATIONS

Khazanov et al. "Lipoplexes prepared from cationic liposomes and mammalian DNA induce CpG-independent, direct cytotoxic effects in cell cultures and in mice." J Gene Med 2006; 8: 998-1007. (Year: 2006).*

Arbor Scientific "Mechanical Wave Complete Bundle", Jan. 1, 2019, Retrieved from the Internet https://www.arborsci.com/products/mechanical-wave-valuepack (retrieved on Aug. 10, 2021).

Search Report and Written Opinion of PCT/EP2021/063610 issued Sep. 13, 2021.

* cited by examiner

DEVICE, METHOD AND COMPOSITION FOR TRANSFECTION OF CELLS WITH NUCLEIC ACIDS

This application is a U.S. national stage of PCT/EP2021/063610 filed on 21 May 2021, which claims priority to and the benefit of Italian Patent Application No. 102020000012055 filed on 22 May 2020, the contents of which are all incorporated herein by reference in their entireties.

The present invention provides a method, a composition and a device for transfection of eukaryotic cells by non-viral vectors. The method and device according to the invention are based on application of a high-frequency oscillatory motion to a solution containing nucleic acids and cationic polymers or lipids to obtain highly efficient transfection complexes.

INTRODUCTION

Transfection involves the delivery of nucleic acids such as DNA or RNA into cells. This technique is common both in clinical practice, for preventive or therapeutic purposes (such as CAR-T therapy), and in basic research, for example in the study of the function of certain genes or for production of a specific protein in the laboratory. Nucleic acid delivery techniques can be classed as viral and non-viral. The former generally use retroviral, adenoviral or adeno-associated viral vectors to transfer genetic material into the cell, but involve drawbacks such as the immunogenicity of the vector and the difficulty of handling it in safe conditions. The most common non-viral systems are based on the use of "naked" nucleic acids, which can be introduced into the cell by physical methods such as electroporation, nucleofection, sonoporation, magnetofection and microinjection, or on the use of non-viral vectors, such as cationic polymers or lipids, which can assemble spontaneously by means of electrostatic interactions with nucleic acids to form particles or complexes (known as "polyplexes" and "lipoplexes" respectively) able to deliver nucleic acids into the cell. In the field of non-viral transfection, Transfection Technologies (TT) use transfection reagents sold in ready-to-use kit form (such as jetPEI® (Polyplus) (Adib, A., Stock, F., & Erbacher, P. (2009). Method for manufacturing linear polyethylenimine (PEI) for transfection purposes and linear PEI obtained with such method. (World Patent No: WO 2009/016507 A3)), Lipofectamine® (Invitrogen) (Gebeyehu, G., Jessee, J. A., Ciccarone, V. C., Hawley-Nelson, P., & Chytil, A. (1994). Cationic lipids. (U.S. Pat. No. 5,334,761)), FuGENE® HD, FuGENE® 6 and ViaFect™ (Promega)), or cationic polymers and cationic lipids to be diluted in aqueous solution at the time of use. Once mixed with nucleic acids, cationic polymers and/or lipids give rise to microparticles and/or nanoparticles with a positive surface charge. Said particles are internalised by the cells, wherein the nucleic acid is subsequently released by the vector and processed by the cell. In view of the current limitations on the use of non-viral technologies, such as the low transfection efficiency and intrinsic toxicity of the technologies currently available, TT research and market are a continuously expanding sector.

STATE OF THE ART

The authors of the present patent application have previously reported an improvement in the efficiency of non-viral transfection by application of vibrations to cell cultures in the presence of complexes formed by nucleic acids and cationic polymers (polyplexes). The published proceedings of congresses held in 2018 (ESCDD 2018, 11-14 Apr. 2018; GNB2018, 25-27 Jun. 2018) and 2019 (35th CBS, 21-24 May 2019; TERMIS AM 2019, 2-5 Dec. 2019) describe the effects induced by vibrations applied to cultured cells on the transfection efficiency of polyethyleneimine (PEI)-based polyplexes administered to said cells. The increased transfection efficiency observed in said systems is attributable to modifications in cell membrane permeability induced by vibrations that promote internalisation of the complexes administered. In these experiments, the complex was prepared by mixing manually, with the aid of a micropipette, an aqueous solution containing the nucleic acid and a solution containing the non-viral vector. Said preparation of the transfection complexes is hereinafter called the "standard preparation". It has been found that the complexes thus formed, when administered to cultured cells subjected to mechanical vibrations, maintain the same physicochemical characteristics (size and charge of the complexes) and transfection ability as the initial preparation.

DESCRIPTION OF THE INVENTION

It has now been found that by applying appropriate mechanical stimulation to an aqueous solution containing cationic polymers or lipids and nucleic acids, in free and uncomplexed form, under suitable conditions a composition is obtained which can be conveniently used for non-viral cell transfection. Said composition has proved surprisingly superior in terms of cell transfection efficiency to transfection complexes obtained by the methods according to the prior art, such as the standard preparation or vortex mixing, and has also proved less toxic than the compositions obtained with commercial kits such as the jetPEI® kit.

The subject of the present invention is therefore a method for preparing a composition for non-viral transfection of cells, comprising the application of an oscillatory motion with a frequency ranging from 100 Hz to 10 kHz and an oscillation amplitude ranging from 200 nm to 2 mm, to an aqueous solution containing, in free or uncomplexed form, a cationic polymer or lipid and the nucleic acid of interest.

The oscillatory motion applied to the solution is preferably uniaxial and it can assume different wave configurations, particularly with a sine, square or triangular waveform.

In a preferred embodiment, the method according to the invention comprises the following steps:

(1) providing, in a suitable container, an aqueous solution containing a cationic polymer or lipid and the nucleic acid of interest;

(2) subjecting said container to an oscillatory motion with an oscillation frequency and amplitude as defined above.

The following conditions for implementation of the method according to the invention, which are independent of one another, are preferred:

the oscillatory motion takes place in a vertical direction;
the frequency of the oscillatory motion ranges from 100 Hz to 10 kHz, preferably from 100 Hz to 1 kHz, and more preferably amounts to 1 kHz;
the oscillation amplitude ranges from 200 nm to 2 mm, preferably from 200 nm to 0.2 mm;
the application time of the oscillatory motion ranges from 1 sec to 30 min, and preferably amounts to 10 seconds.

The cationic polymers used in the method according to the invention are known to the skilled person because they are commonly used for non-viral gene delivery applications [Bono N. et al., *Non-viral in vitro gene delivery: it is now

*time to set the bar!*. Pharmaceutics 2020, 12(2), 183; Malloggi C. et al., *Comparative evaluation and optimization of off-the-shelf cationic polymers for gene delivery purposes*. Polym. Chem. 2015, 6, 6325-6339; Mintzer M. A. and Simanek E. E. Nonviral vectors for gene delivery. Chem. Rev. 2009, 109, 259-302].

The cationic polymer is preferably selected from linear or branched polyethylenimine (PEI) (lPEI or bPEI), polyamidoamine (PAMAM), polylysine in forms D and L (PDL and PLL), chitosan, poly(dimethylaminoethyl methacrylate) (PDMAEMA) and poly(diethylaminoethyl methacrylate) (PDEAEMA).

The cationic lipid is selected from those commonly used to prepare lipoplexes [Simões S. et al., *Cationic liposomes for gene delivery*. Expert Opin. Drug Deliv. 2005, 2, 237-254; de Ilarduya C. T. et al., *Gene delivery by lipoplexes and polyplexes*. Eur. J. Pharm. Sci. 2010, 40(3), 159-170], and in particular from the following: 1,2-dioleoyl-3-trimethylammonium propane (DOTAP), 1,2-di-O-octadecenyl-3-trimethylammonium propane (DOTMA), dioctadecylamidoglycylspermine (DOGS), dimethyl-dioctadecyl-ammonium bromide (DDBA), 3β[N—(N',N'-dimethylaminoethane)carbamoyl]cholesterol (DC-chol), 2,3-dioleyloxy-N-[2(sperminecarb oxami do)ethyl]-N,N-dimethyl-1-propanaminium trifluoroacetate (DOSPA), 1,2-dimyristyloxy-propyl-3-dimethyl-hydroxyethyl ammonium bromide (DMRIE), and cetyltrimethyl-ammonium bromide (CTAB).

The cationic polymer or lipid is generally prepared in aqueous solutions with different salinities, such as deionised water, HEPES buffer solution, optionally with the addition of glucose (HGB), or saline solution.

The nucleic acid generally consists of DNA molecules, such as plasmid DNA (pDNA)), or RNA molecules, such as siRNA, miRNA, shRNA or mRNA.

The nucleic acid is preferably used in the form of an aqueous solution in Tris/EDTA or HEPES buffer. The solution is preferably DNAse- and RNAse-free.

The solution containing the nucleic acid is added to the solution containing the cationic lipid or polymer, or vice versa. The solution containing the nucleic acid is preferably added to the solution containing the cationic polymer or lipid.

The volumetric ratio between the two solutions (volume/volume) can range between 1:100 and 100:1, preferably between 1:10 and 10:1, and more preferably amounts to 10:1 (polymer or lipid:nucleic acid).

The container containing the cationic polymer or lipid and the nucleic acid is generally a laboratory test tube with a capacity ranging from 0.1 mL to 50 mL, preferably from 0.1 mL to 1.5 mL.

Another aspect of the invention relates to a composition for non-viral cell transfection obtainable by a method as defined above.

A further aspect of the invention relates to a method for transfection of cultured cells, which comprises contacting the cells with said composition. Cell lines or primary cells obtained from explants, including adherent cells and cells in suspension, can be transfected. In a preferred embodiment, the cell transfection method comprises the following steps:
 (a) providing a cell culture containing a culture medium;
 (b) adding the composition according to the invention to the culture medium.

A further aspect of the invention relates to a device for preparing a composition for non-viral transfection according to the method described herein. Said device comprises a wave generator, preferably a sine wave generator, of the required frequency and amplitude, and an electromechanical actuator fitted with a drive shaft, at one end whereof a test tube housing is fitted in such a way that the voltage produced by the generator is converted by the actuator to oscillatory motion, preferably of uniaxial type, which is transmitted to the test tube via the drive shaft.

As indicated above, the test tube can have a capacity ranging from 0.1 mL to 50 mL, preferably from 0.1 mL to 1.5 mL.

The transfection composition obtained with the method and device according to the invention has exhibited transfection efficiency 10 to 100 times greater than that of conventional techniques, based on mixing polymers or lipids and nucleic acids with manual techniques (ie. using a micropipette) or with vortex mixers, as well as lower inter- and intra-operator variability and therefore greater reproducibility of the results.

The transfection method according to the invention exhibits an efficiency comparable with those of the commercial kits commonly used in the laboratory, such as jetPET®, Lipofectamine® and FuGENE® HD, but lower toxicity (lower than 10% in cell lines and 25% in primary cells, respectively).

Further advantages are represented by the speed of implementation of the method according to the invention, which allows transfection compositions to be prepared in a few seconds, and its simplicity of use compared with other transfection systems.

The examples below illustrate the invention in greater detail.

EXAMPLE 1—DEVICE

Figure 1:
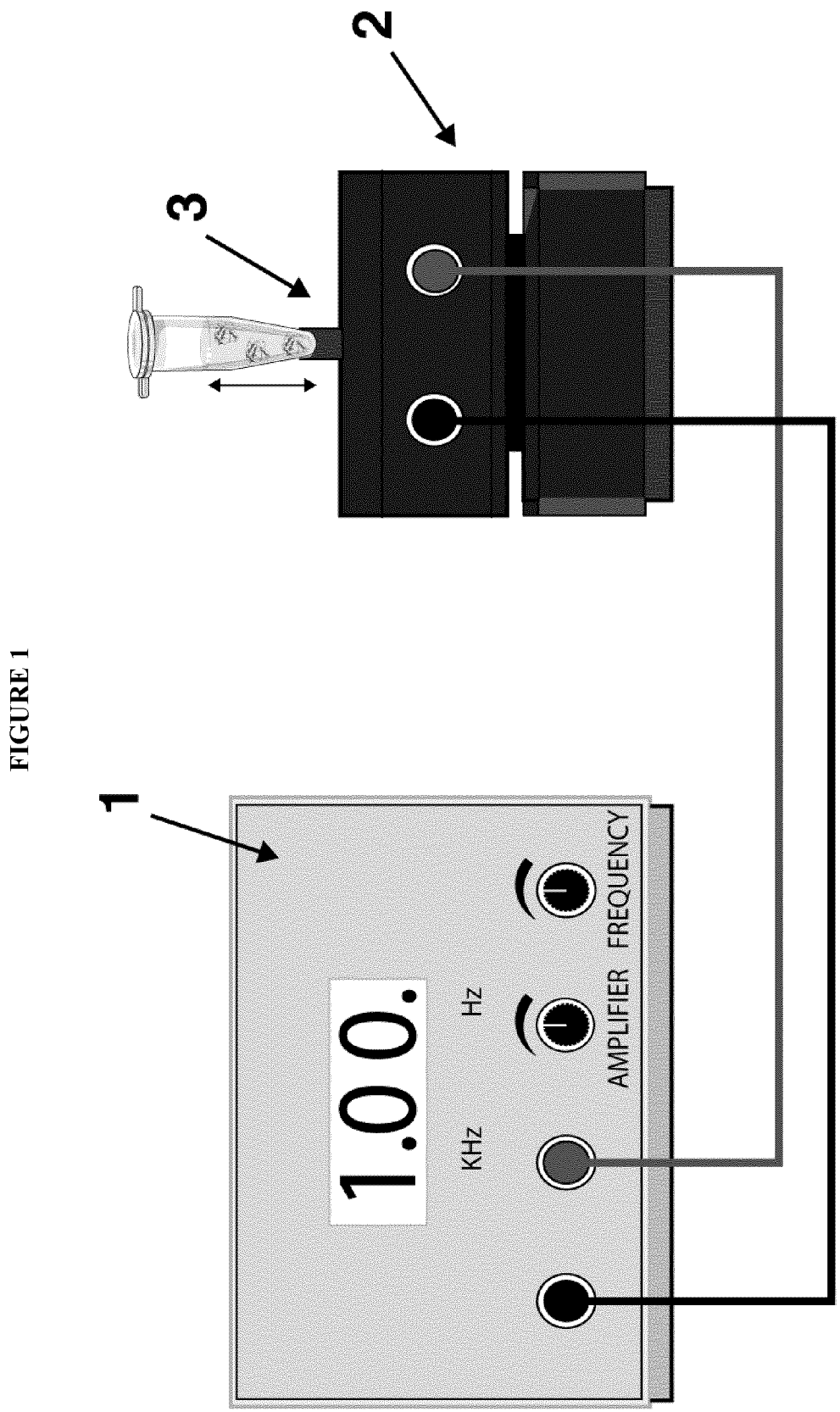
FIG. 1: Scheme of device used; sine, square or triangular wave generator with controlled amplitude and frequency (1), mechanical actuator that converts the input voltage into motion along z-axis (2), laboratory test tube housing which transmits the oscillatory uniaxial motion to a test tube (3).
Figure 2:
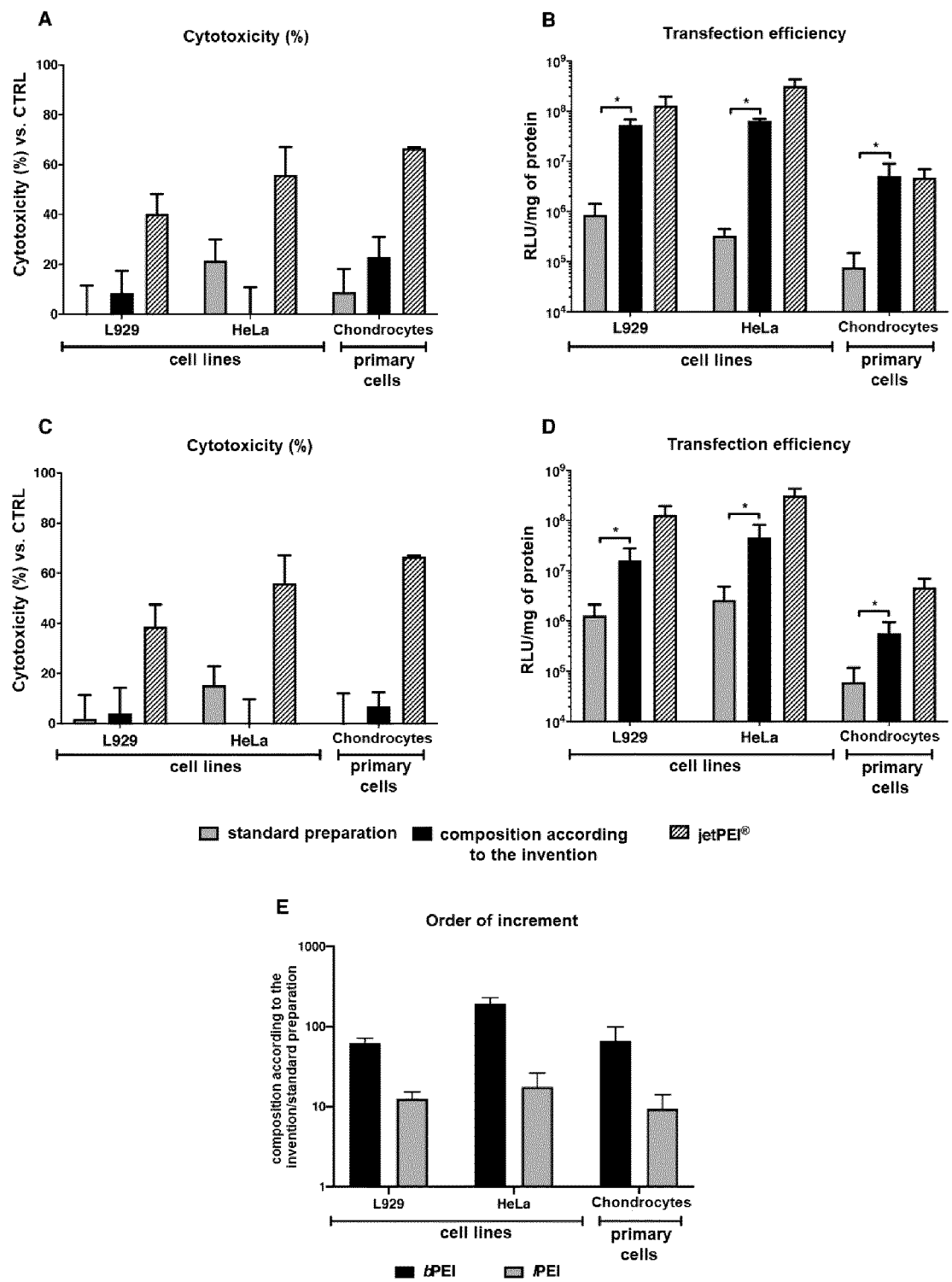
FIG. 2: Results, expressed in terms of cytotoxicity (A, C) and transfection efficiency (B, D), obtained in vitro on L929 and HeLa cell lines and on bovine chondrocytes (primary cells) with complexes based on plasmid DNA (pGL3) and the cationic polymer polyethylenimine (PEI); A, B) PEI in branched form; C, D) PEI in linear form obtained by the method according to the invention and standard preparation; E) Results expressed in terms of increased transfection efficiency of complexes based on plasmid DNA (pGL3) and PEI (in branched form (bPEI) and linear form (lPEI)) prepared by the method according to the invention vs. the standard preparation. The data are expressed as mean±standard deviation) (n≥3). *$p<0.05$.
Figure 3:
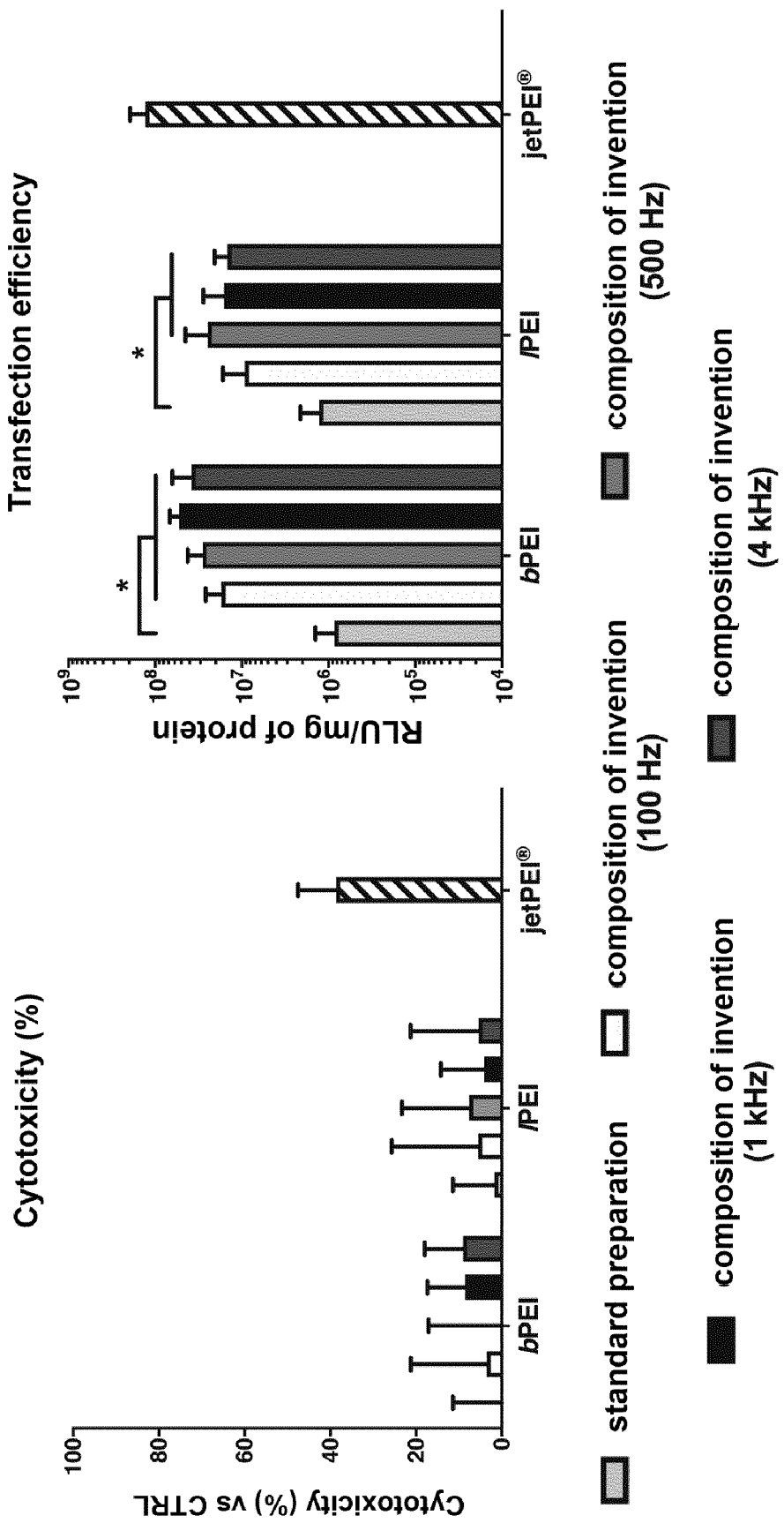
FIG. 3: Cytotoxicity and transfection efficiency on L929 cells of (i) a composition according to the invention obtained by varying the mixing frequency of cationic polymer and nucleic acid, (ii) a standard preparation obtained by manual mixing, and (iii) a commercial kit (jetPEI®). The data are expressed as mean±standard deviation (n≥3). *$p<0.05$ vs. standard preparation.
Figure 4:
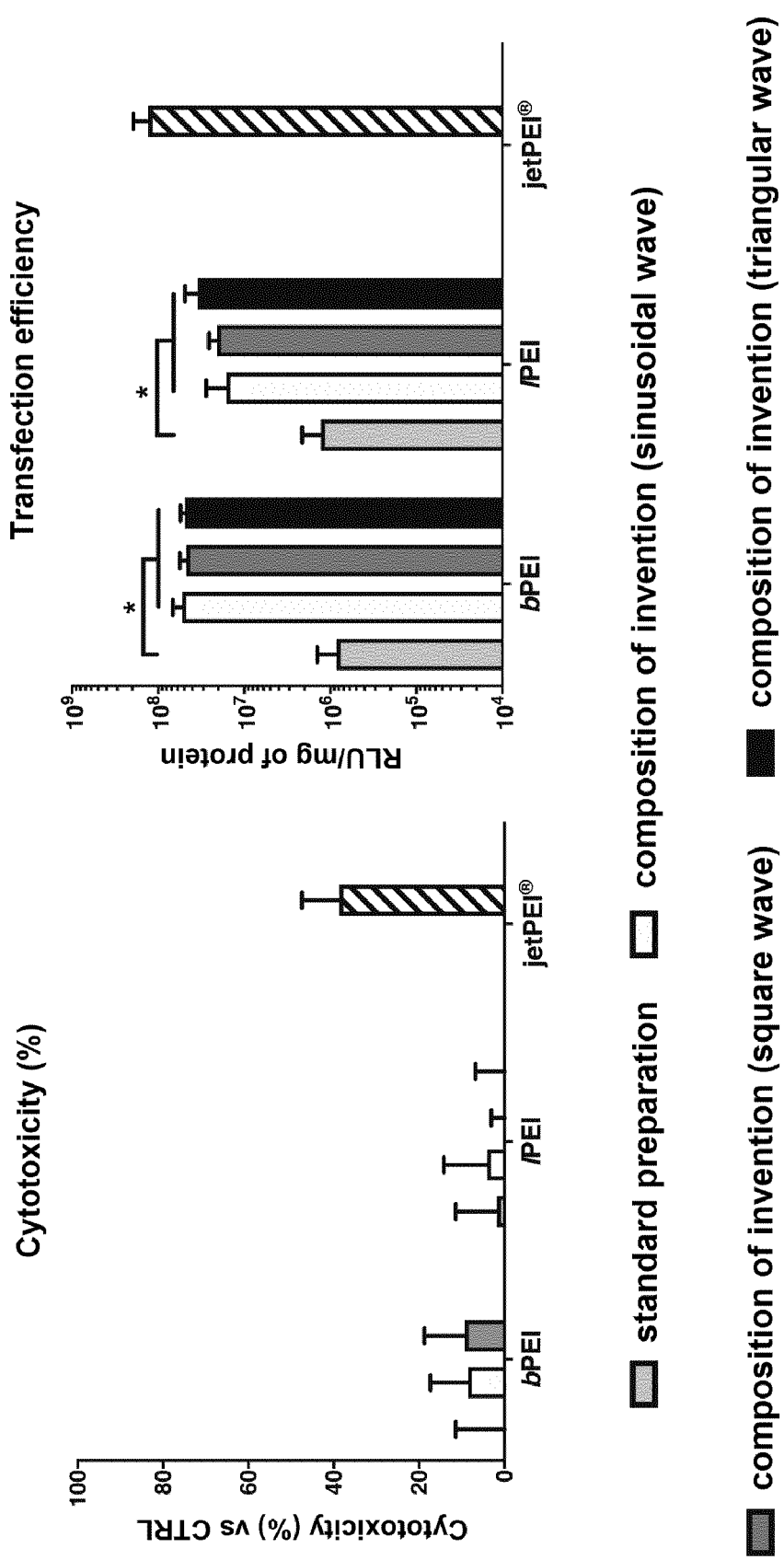
FIG. 4: Cytotoxicity and transfection efficiency on L929 cells of (i) a composition according to the invention obtained by vertical mixing of cationic polymer and nucleic acid using various waveforms, (ii) a standard preparation obtained by manual mixing, and (iii) a commercial kit (jetPEI®). The data are expressed as mean±standard deviation (n≥3). *$p<0.05$ vs. standard preparation.
Figure 5:
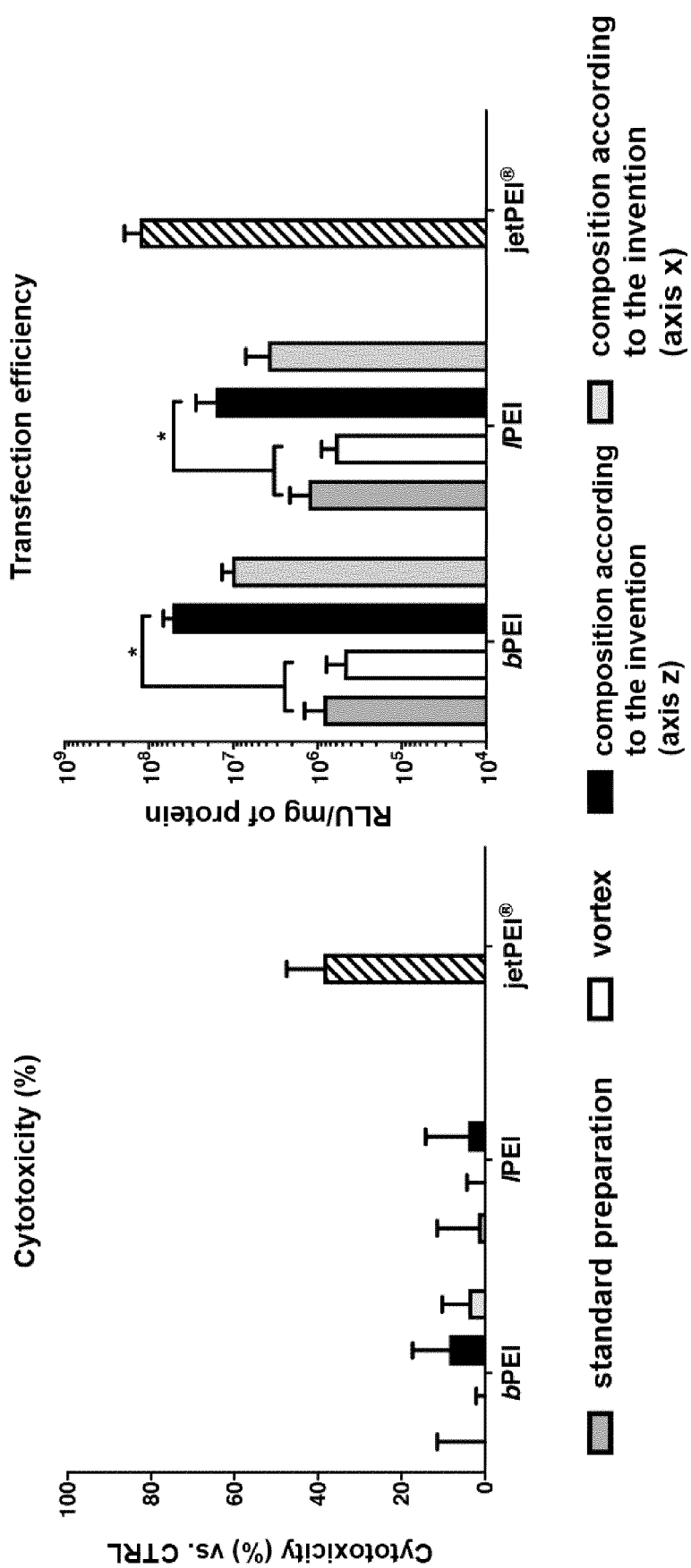
FIG. 5: Cytotoxicity and transfection efficiency on L929 cells of (i) a composition according to the invention obtained by vertical and horizontal mixing of cationic polymer and nucleic acid, (ii) a standard preparation obtained by manual or vortex mixing, and (iii) a commercial kit (jetPEI®). The data are expressed as mean±standard deviation) (n≥3). *p<0.05.

A bench prototype device was assembled, consisting of an electromechanical actuator or mechanical wave driver (component 2 in FIG. 1) which converts input voltage into uniaxial motion of a drive shaft. Said component is coupled to a sine, square or triangular wave generator (component 1 in FIG. 1), which allows its control in terms of frequency (frequency range: 100 Hz-10 kHz) and amplitude of motion (displacement range: 200 nm-2 mm). The optimum conditions of use are: i) input wave type: sine wave; ii) direction of motion: vertical (z-axis); iii) frequency: 1 kHz, iv) displacement: 200 nm. Both components are marketed by Arbor Scientific (https://www.arborsci.com/) as demonstrators for toys or teaching purposes for the production of harmonic waves. However, other devices already available on the market or developed ad hoc, having a test tube housing for the preparation of different transfection compositions in parallel, can be used. In the prototype used, the shaft of the mechanical actuator was suitably fitted with a laboratory test tube housing (component 3—FIG. 1), to which it integrally transmits the drive shaft motion and allows controlled mixing of the transfection reagents contained in the laboratory test tube. In particular, the application of high-frequency oscillatory motion along the z-axis allows controlled mixing of cationic polymers or lipids and nucleic acids, thus producing nanoparticles and microparticles or transfection complexes in a reproducible, controlled way (FIG. 1). The oscillatory motion can be suitably varied in terms of displacement and frequency of oscillation of the test tube.

EXAMPLE 2—PREPARATION OF TRANSFECTION COMPOSITION (i) A solution of 25 kDa cationic polymer polyethylenimine (PEI, in its linear form (lPEI) and branched form (bPEI)) was prepared at a concentration of 0.86 mg/mL, corresponding to an amine concentration ([N]) of 20 mM, in a 10 mM HEPES buffer solution at pH 7.5. Alternatively, the cationic polymer can be dissolved in deionised water ($dH_2O$); saline solution (150 mM NaCl; pH=7.5); HGB (10 mM HEPES+5% (weight/volume) glucose; pH 7).

The solution was stored at 4° C. until use.

(ii) A solution of plasmid DNA containing the gene that encodes for the intracellular protein luciferase (pGL3-Control Vector, 5.2 kbp) was prepared separately at a concentration of 0.25 µg/µL in sterile aqueous solution 0.1×TE (10 mM Tris-HCl, pH 7.5, 1 mM EDTA). If siRNA, miRNA, shRNA or mRNA is used, the nucleic acid can be dissolved in sterile 1×siMAX buffer (6 mM HEPES, 20 mM KCl, 0.2 mM $MgCl_2$, pH 7.3) (Eurofins Genomics, Germany) at a concentration of 0.1 µg/µL.

The solution was stored at −20° C. until use.

(iii) All reagents were heated to the desired temperature before use.

A preselected volume of cationic polymer solution was transferred to a test tube to which a preselected volume of pDNA solution was added in a 10:1 volumetric ratio (v/v). Specifically, an amount of polymer containing a number of moles of amines such as to form polyplexes with an N/P ratio (ie. the ratio between the number of moles of amines of the cationic polymer and the number of moles of phosphates of the nucleic acid) of 30 was used.

(iv) The test tube was inserted into the housing suitably connected to the shaft of the mechanical actuator of the device (FIG. 1).

(v) The wave generator was operated at a mixing frequency of 1 kHz for 10 sec.

(vi) The resulting solution was immediately administered to the cells previously seeded in the culture plate.

EXAMPLE 3—PREPARATION OF TRANSFECTION COMPOSITION AT VARIOUS FREQUENCIES

The process was conducted as in the previous example, steps (i)-(iii).

The solution obtained in step (iii) was mixed manually with a micropipette for 10 sec and incubated for 20 min.

Alternatively, the solution was mixed by the method according to the invention at various mixing frequencies (100 Hz, 500 Hz, 1 kHz and 4 kHz) for 10 sec.

The resulting solution was administered to cells previously seeded in the culture plate, as described in the example 6.

EXAMPLE 4—PREPARATION OF TRANSFECTION COMPOSITION USING VARIOUS WAVEFORMS

The process was conducted as in the previous example, steps (i)-(iii).

The solution obtained in step (iii) was mixed manually with a micropipette for 10 sec and incubated for 20 min.

Alternatively, the solution was mixed by the method according to the invention. The waveform of the generator was suitably set as a sine, square or triangular wave, and the generator was operated at a stimulation frequency of 1 kHz for 10 sec.

The resulting solution was administered to cells previously seeded in the culture plate, as described in the example 6.

EXAMPLE 5—PREPARATION OF COMPARATIVE STANDARD

The process was conducted as in the example 2, steps (i)-(iii).

The solution obtained in step (iii) was mixed manually with a micropipette for 10 sec and incubated for 20 min.

Alternatively, the solution was mixed with a vortex.

The resulting solution was administered to cells previously seeded in the culture plate.

EXAMPLE 6—TRANSFECTION EXPERIMENTS

Cell lines L929 (murine fibroblasts from subcutaneous connective tissue, CCL-1) and HeLa (human epithelial cells from ovarian cancer, CCL-2) were purchased from the American Type Culture Collection (ATCC®, Manassas, VA, USA). The primary chondrocytes were obtained from bovine metacarpophalangeal joint as previously described

[Candiani G. et al., *Chondrocytes response to high regimen of cyclic hydrostatic pressure in 3-dimensional engineered constructs*, Int. J. Artif. Organs. 2008, 31(6), 490-499]. The cells were seeded in 96-well culture plates at a cell density of $2\times10^4$ cells/cm$^2$ and cultured at 37° C. in a humidified atmosphere and 5% (volume/volume) $CO_2$ (hereinafter called "standard culture conditions") in culture medium (Dulbecco's Modified Eagle's Medium (DMEM) completed with 10% (volume/volume) foetal bovine serum (FBS), 10 mM HEPES, 100 U/L penicillin, 0.1 mg/mL streptomycin, 1 mM sodium pyruvate and 2 mM glutamine (hereinafter called "complete medium"). 24 hours after seeding, 160 ng/cm$^2$ of pGL3 (in the case of cell lines) and 320 ng/cm$^2$ of pGL3 (in the case of primary cells) were complexed in 10 mM HEPES buffer with lPEI or bPEI using the method according to the invention or standard preparation as described in examples 2-4 and 5, respectively. Complexes prepared with a commercial kit (ie. jetPEI®) were obtained by mixing 780 ng/cm$^2$ of pGL3 with the commercial transfectant solution by the procedures reported by the supplier and used as internal reference. The complexes were dispensed to the cells in 100 μL/well of complete medium, and the cells were incubated for 24 hours under standard culture conditions.

To compare the invention with the state of the art, L929 cells were treated with polyplexes obtained by the method of invention and by standard preparation, respectively, and they were subsequently subjected to mechanical stimulation with vibrations for 5 min at 1 kHz.

The cytotoxicity of the polyplexes was evaluated 24 hours after transfection by Alamar Blue® assay. Specifically, the medium in each well was eliminated and replaced with 100 μL/well of complete medium containing 1:9 (volume/volume) of resazurin. The cells were incubated for 2 hours under standard culture conditions, and the fluorescence was then read with a Synergy H1 multiplate reader (BioTek, Italy), using as excitation and emission wavelengths $\lambda_{excitation}$=540 nm and $\lambda_{emission}$=595 nm respectively. Cytotoxicity was calculated as follows:

cytotoxicity(%)=100%−viability(%)

wherein 100% was assigned to the untransfected cells (CTRL).

The transfection efficiency was determined by measuring the luciferase activity. Specifically, after being washed with Phosphate Buffered Saline (PBS), the cells were lysed with 110 μL/well of lysis solution (Promega, Italy) and subjected to freezing-thawing cycles to promote lysis.

20 μL of cell lysate was then mixed with 50 μL of Luciferase Assay reagent (Promega, Italy) to measure luciferase activity. The chemiluminescence signal (Relative Light Unit, RLU) of each sample was acquired with a Synergy H1 multiplate reader and normalised to the total protein quantity, calculated by BCA assay (ThermoFisher, Italy). Transfection efficiency was expressed as RLU/mg of protein. Each experiment was conducted at least in triplicate (n≥3), and the data are expressed as mean±standard deviation.

The results shown in FIGS. 2-5 clearly indicate that the composition according to the invention: (1) has greater transfection efficiency than the standard preparation obtained by manual or vortex mixing, (2) exhibits lower toxicity than the commercial kit, and (3) is effective on different types of cell lines as well as on primary cells.

Figure 6:
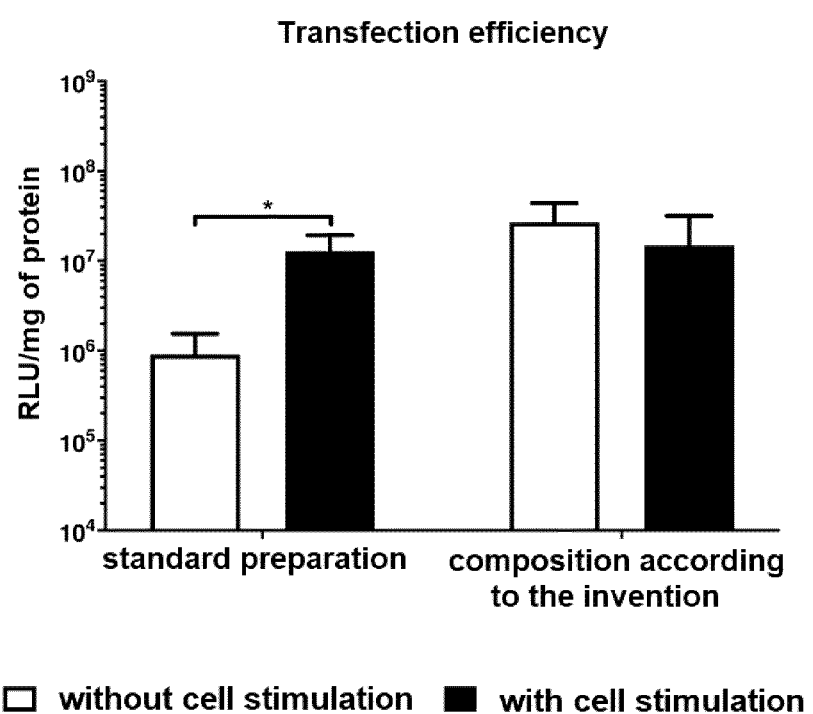
FIG. 6: Transfection efficiency on L929 cells of (i) a composition according to the invention and (ii) a standard preparation in the absence or presence of cell stimulation with high-frequency vertical oscillatory uniaxial motion. The data are expressed as mean±standard deviation) (n≥3). *p<0.05.

Using the same experimental model, the system according to the invention was also compared with the standard method applied to cell cultures in the presence or absence of cell stimulation with high-frequency oscillatory motion. As illustrated in FIG. 6, polyplexes obtained by the method of invention exhibit high transfection efficiency regardless of the presence of mechanical-vibrational cell stimulation, whereas with the standard preparation, comparable efficiency to that of the method of invention is only obtained with mechanical-vibrational stimulation of the cells. This result demonstrates that unlike the standard preparation, the system according to the invention guarantees high transfection efficiency with no need to pre-treat or stimulate the cells, thus avoiding additional toxicity problems or cell phenotype modifications.

The invention claimed is:

1. A method for preparing a composition for non-viral transfection of cells with nucleic acids, said method comprising
    applying an oscillatory motion with frequency ranging from 500 Hz to 10 kHz and oscillation amplitude ranging from 200 nm to 2 mm, to a solution containing, in uncomplexed form, a cationic polymer or lipid and the nucleic acids.

2. The method according to claim 1, which comprises the following steps:
    (i) providing, in a suitable container, an aqueous solution containing the cationic polymer or lipid and the nucleic acids;
    (ii) applying an oscillatory motion with frequency ranging from 500 Hz to 10 kHz and oscillation amplitude ranging from 200 nm to 2 mm to said container.

3. The method according to claim 2, wherein the container is a test tube having a capacity ranging from 0.1 mL to 50 mL.

4. The method according to claim 2, wherein the container is a test tube having a capacity ranging from 0.1 mL to 1.5 mL.

5. The method according to claim 1, wherein the oscillatory motion is uniaxial.

6. The method according to claim 1, wherein the oscillatory motion is along the vertical axis.

7. The method according to claim 1, wherein the oscillatory motion has a sine, square or triangular waveform.

8. The method according to claim 1, wherein the oscillatory motion is applied for a time ranging from 1 sec to 30 min.

9. The method according to claim 1, wherein the cationic polymer is selected from linear or branched polyethylenimine (lPEI and bPEI), polyamidoamine (PAMAM), D- or L-polylysine (PDL and PLL), chitosan, poly(dimethylaminoethyl methacrylate) (PDMAEMA) and poly(diethylaminoethyl methacrylate) (PDEAEMA).

10. The method according to claim 1, wherein the cationic lipid is selected from 1,2-dioleoyl-3-trimethylammonium propane (DOTAP), 1,2-di-O-octadecenyl-3-trimethylammonium propane (DOTMA), dioctadecylamidoglycylspermine (DOGS), dimethyl-dioctadecylammonium bromide (DDBA), 3ß-[N—(N',N'-dimethylaminoethane)-carbamoyl] cholesterol (DC-chol), 2,3-dioleyloxy-N-[2 (sperminecarboxamido)ethyl]-N,N-dimethyl-1-propanaminium trifluoroacetate (DOSPA), 1,2-dimyristoyloxy-propyl-3-dimethylhydroxyethyl ammonium bromide (DMRIE), and cetyltrimethyl-ammonium bromide (CTAB).

11. The method according to claim 1, wherein the frequency of the oscillatory motion ranges from 500 Hz to 1 kHz.

12. The method according to claim 1, wherein the amplitude of the oscillatory motion ranges from 200 nm to 0.2 mm.

13. The method according to claim 1, wherein the frequency of the oscillatory motion is equal to 1 kHz.

* * * * *